United States Patent
Colvin, Jr. et al.

(10) Patent No.: US 7,190,445 B2
(45) Date of Patent: *Mar. 13, 2007

(54) HIGH PERFORMANCE FLUORESCENT OPTICAL SENSOR

(75) Inventors: Arthur E. Colvin, Jr., Mt. Airy, MD (US); Steven J. Walters, Ellicott City, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/165,129

(22) Filed: Jun. 24, 2005

(65) Prior Publication Data

US 2005/0237518 A1    Oct. 27, 2005

Related U.S. Application Data (63) Continuation of application No. 10/316,188, filed on Dec. 11, 2002, now Pat. No. 6,940,590.

(60) Provisional application No. 60/338,647, filed on Dec. 11, 2001.

(51) Int. Cl.
  *G01J 1/42*   (2006.01)
  *G01N 21/01*  (2006.01)

(52) U.S. Cl. ............... 356/218; 356/436; 356/244; 250/458.1; 436/164; 436/527; 422/82.05

(58) Field of Classification Search ............ 356/218, 356/436, 244, 410, 417, 317, 318, 234; 385/12, 385/129–131; 250/458.1, 459.1; 422/82.05, 422/82.08; 436/164, 527
See application file for complete search history.

(56) References Cited

U.S. PATENT DOCUMENTS

| | | |
|---|---|---|
| 4,755,667 A | 7/1988 | Marsoner et al. |
| 4,906,100 A | 3/1990 | Rice et al. |
| 5,018,866 A | 5/1991 | Osten |
| 5,030,009 A | 7/1991 | Ando et al. |
| 5,039,490 A | 8/1991 | Marsoner et al. |
| 5,439,647 A | 8/1995 | Saini |
| 5,453,248 A | 9/1995 | Olstein |
| 5,517,313 A | 5/1996 | Colvin, Jr. |
| 5,894,351 A | 4/1999 | Colvin, Jr. |

(Continued)

FOREIGN PATENT DOCUMENTS

EP    0834734 A2    4/1998

(Continued)

*Primary Examiner*—Layla G. Lauchman
(74) *Attorney, Agent, or Firm*—Rothwell, Figg, Ernst & Manbeck (57) ABSTRACT

An optical sensor device for determining the presence or concentration of an analyte, contains a waveguide disposed over a light source and a light detector mounted on a surface of a substrate and separated by an internal baffle, wherein the waveguide has a thickness corresponding to a far field emission point of the light source as determined by a light shielding baffle between the light source and light detector. An analyte indicator matrix is disposed on the outer surface of the waveguide. The sensor device geometry takes advantage of only direct illumination of the indicator matrix, and direct collection of indicator matrix illumination, without any significant reflection by said waveguide. Undesirable light noise generated by the light source passes directly out of the device through the waveguide.

4 Claims, 6 Drawing Sheets

U.S. PATENT DOCUMENTS

| | | |
|---|---|---|
| 5,910,661 A | 6/1999 | Colvin, Jr. |
| 5,917,605 A | 6/1999 | Colvin, Jr. |
| 5,919,710 A | 7/1999 | Gord et al. |
| 6,024,923 A | 2/2000 | Melendez et al. |
| 6,045,756 A | 4/2000 | Carr et al. |
| 6,110,749 A * | 8/2000 | Obremski et al. .......... 436/527 |
| 6,111,248 A | 8/2000 | Melendez et al. |
| 6,119,031 A | 9/2000 | Crowley |
| 6,304,766 B1 | 10/2001 | Colvin, Jr. |

FOREIGN PATENT DOCUMENTS

| | | |
|---|---|---|
| WO | 9706422 A1 | 2/1997 |
| WO | 0013003 A1 | 3/2000 |

* cited by examiner

HIGH PERFORMANCE FLUORESCENT OPTICAL SENSOR

CROSS-REFERENCE TO RELATED APPLICATION

This application is a continuation of application Ser. No. 10/316,188 filed Dec. 11, 2002 now U.S. Pat No. 6,940,590 which claims priority under 35 U.S.C. §119(e) to Provisional Application Ser. No. 60/338,647 filed Dec. 11, 2001.

BACKGROUND OF THE INVENTION

1. Field of the Invention

This invention relates generally to sensor devices for detection of electromagnetic emissions from an indicator having an analyte of interest permeating therethrough, wherein the characteristics of the emissions vary as a function of the concentration of the analyte. More particularly, the invention relates to improvements in the design and performance of such sensor devices.

2. Background Art

U.S. Pat. No. 5,517,313, the disclosure of which is incorporated herein by reference, describes a fluorescence sensing device comprising a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light from the indicator molecules to reach the photodetector, while filtering out scattered incident light from the light source. An analyte is allowed to permeate the fluorescent matrix, changing the fluorescent properties of the indicator material in proportion to the amount of analyte present. The fluorescent emission is then detected and measured by the photodetector, thus providing a measure of the amount or concentration of analyte present within the environment of interest.

One advantageous application of a sensor device of the type disclosed in the '313 patent is to implant the device in the body, either subcutaneously or intravenously or otherwise, to allow instantaneous measurements of analytes to be taken at any desired time. For example, it is desirable to measure the concentration of oxygen in the blood of patients under anesthesia, or of glucose in the blood of diabetic patients.

Since the invention of the device described in the '313 patent, the present inventors have developed a number of design improvements which have significantly enhanced the performance, reliability and longevity of optical sensor devices of the type described in the '313 patent.

In particular, because of the size and weight restrictions placed on such sensor devices especially for in-vivo or in-situ applications, it is important to maximize the efficiency of the available indicator matrix in order to obtain a more reliable and accurate measurement signal, while minimizing power consumption and heat generation. Additionally, the sensor device design should permit cost-effective high volume manufacturing at a reasonable selling price. Further, maximizing the longevity of the device is desirable especially where the device must be implanted in the body for in-situ detection of bioanalytes.

SUMMARY OF THE INVENTION

In accordance with an aspect of the present invention, an optical sensor device for determining the presence or concentration of an analyte, is provided, including a substrate; a light-shielding baffle layer formed on the substrate, and containing at least two cavities therein; a light source for emitting light primarily of a preselected wavelength upon energization, mounted on a surface of the substrate in one of the cavities; a light detector for detecting light incident thereon and generating an electrical signal responsive thereto, mounted adjacent to the light source on the surface of the substrate in another of the cavities, and being separated therefrom by the light shielding baffle; a waveguide formed over the light source and the light detector, wherein the light source-containing cavity is filled with a transparent epoxy material having the same refractive index as the waveguide, such that the light source may be considered to be located "within" the waveguide; the waveguide having a mean thickness corresponding to a far field emission point of the light source as determined by the light source's position relative to the light shielding baffle, the intrinsic emission profile of the light source, or a combination of the relative position and intrinsic emission profile; and an analyte-permeable indicator matrix disposed on an outer surface of the waveguide, the fluorescent matrix containing fluorescent indicator molecules whose fluorescence is attenuated or enhanced by the presence of analyte in said fluorescent matrix, the preselected and fluorescent indicator molecule being selected such that the wavelength emitted by the light source excites fluorescence in the indicator molecules; wherein the light detector generates an electrical signal responsive to fluorescent light incident thereon emitted by said fluorescent indicator molecules. The photodetector cavity is filled with a color-doped material which acts as a filter to substantially block from said photodetector emission wavelengths other than desired peak emission wavelengths from the indicator molecules. The fill-in material for both the photodetector and the light source cavities can be an epoxy or other polymeric material.

BRIEF DESCRIPTION OF THE DRAWINGS

The invention will be more fully understood with reference to the following detailed description of a preferred embodiment in conjunction with the accompanying drawings, which are given by way of illustration only and thus are not limitative of the present invention, and wherein.

DETAILED DESCRIPTION OF THE PREFERRED EMBODIMENT

Figure 1A:
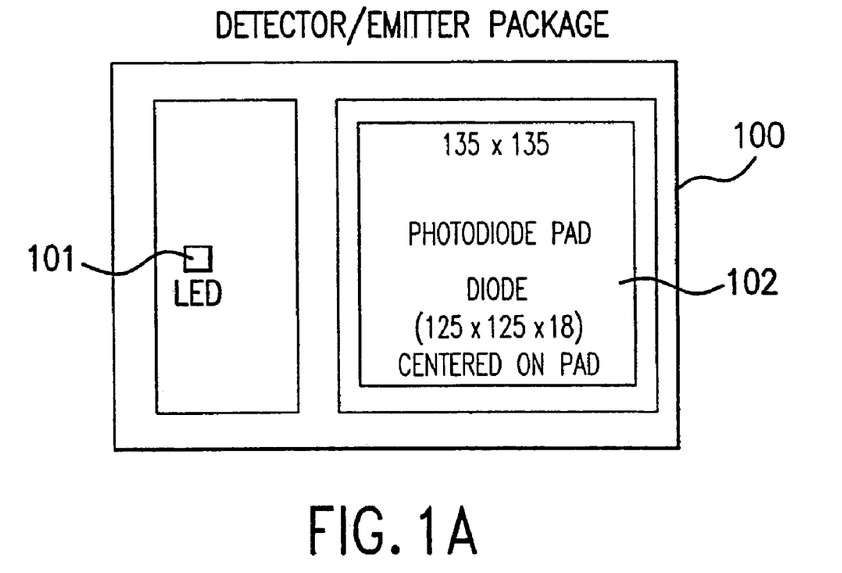
FIG. 1A is a top view of an optical sensor device according to one embodiment of the present invention.
Figure 1B:
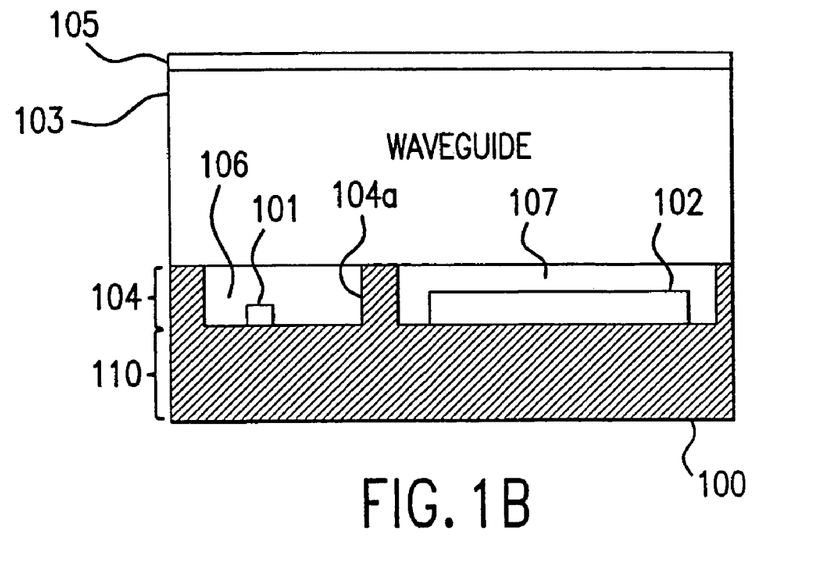
FIG. 1B is a side view of the optical sensor device of FIG. 1A.

FIGS. 1A and 1B show an embodiment of an optical sensor device according to the present invention. The device includes a light source, such as LED 101, and a light detector, such as photodiode 102, mounted on a substrate 100. The light source and light detector are encapsulated by a waveguide 103, the outer surface of which is provided with a fluorescence-indicator matrix 105 containing analyte-indicator molecules. The matrix 105 is disposed on the outer surface of the waveguide 103 in one of a variety of different ways, such as by deposition, coating, adhesion, etc. The light source 101 and light detector 102 are separated from each other by an internal baffle 104a, which is part of a baffle layer portion 104 of the substrate 100. The baffle portion 104 may be formed either separately from the substrate 100 or integrally with formation of the substrate with subsequent etching or masking of the cavities.

Baffle layer 104 can be formed over the base layer 110 of the substrate 100 to define a number of cavities into which the light source and photodetector are placed to be mounted on the substrate. Prior to forming the waveguide layer 103 over the cavities, the light source cavity is filled with a transparent epoxy or other polymeric material 106, which preferably has substantially the same refractive index as the waveguide 103. The fill-in material 106 may be, but is not required to be, the same material used for the waveguide 103.

The photodetector cavity is filled with a color-doped epoxy or polymeric material 107, which functions as a filter to block direct or reflected light from the light source 101 from impinging on the photodetector 102. The color of the material 107 is selected to correspond to the peak emission of the indicator molecules.

Alternately, the photodetector cavity can be filled with the color-doped material, and thereafter the light source cavity can be filled simultaneously with the formation of the waveguide layer, such that the light source will be embedded within an integrally formed waveguide layer.

Additionally, instead of being filled with a clear material, the light source cavity also may be filled with a color-doped material, the color of which is selected to substantially block all wavelength emissions from the light source other than the desired, peak wavelength emission.

Figure 2A:
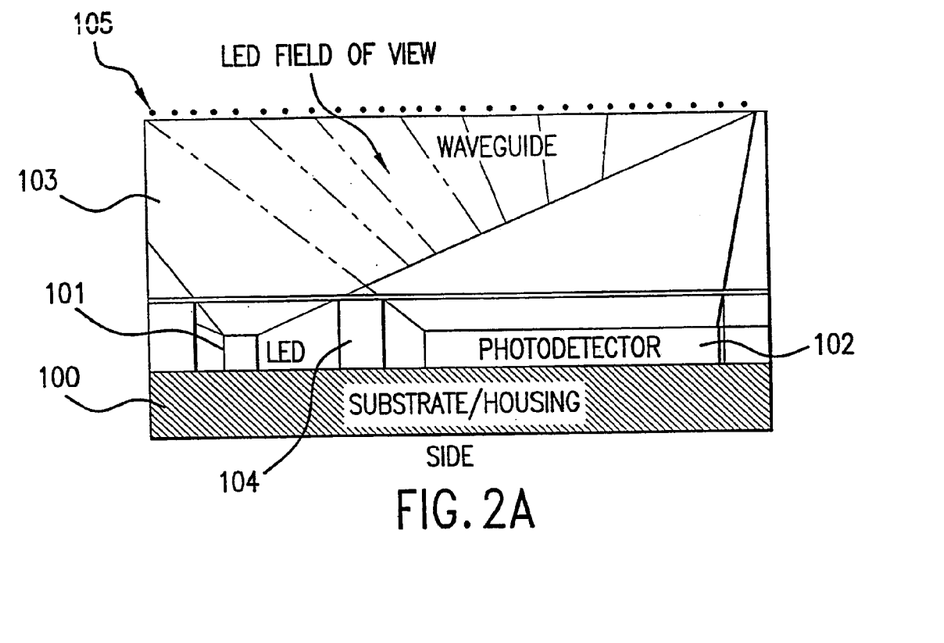
FIG. 2A is a side view of the optical sensor device of FIGS. 1A–1B, illustrating excitation and indicator response fields of view.
Figure 2B:
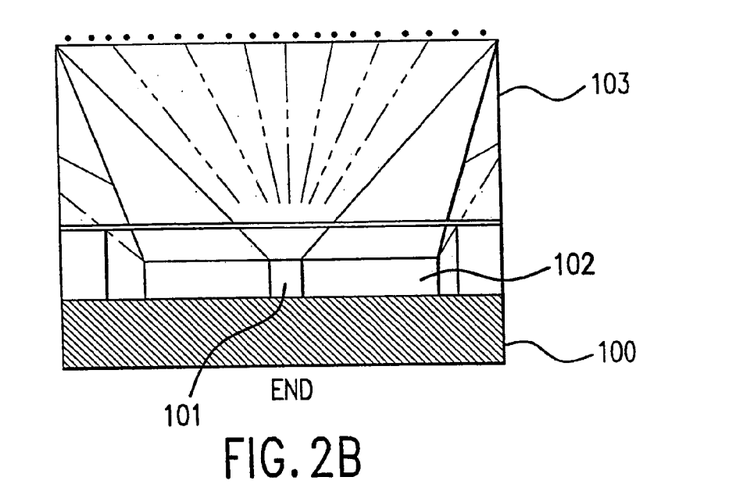
FIG. 2B is an end view of FIG. 2A.
Figure 6:
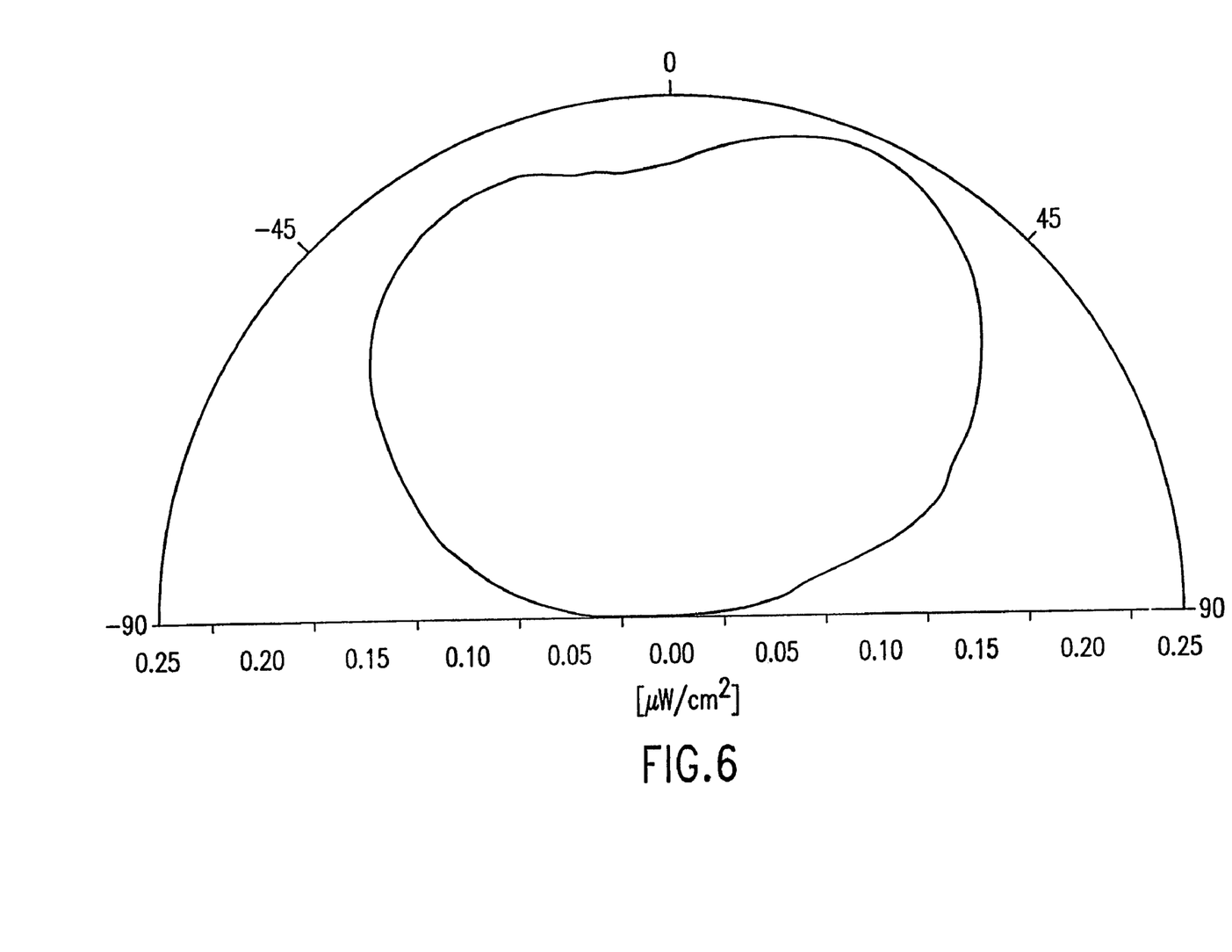
FIG. 6 is a graph showing the light emission profile of an LED light source suitable for use with the optical sensor device according to the present invention.

As shown in FIGS. 2A and 2B, the configuration of the optical sensor device according to the invention is based on achieving substantially only a direct illumination by the light source 101 of substantially the entire outer surface of the waveguide 103, which is provided with fluorescence indicator matrix 105, and substantially only a direct collection on the surface of the photodetector 102 of the responsive emission from the indicator matrix 105. Internal baffle 104 prevents stray illumination of the photodetector 102 by the light source 101. The light emission profile geometry of the LED light source is shown in FIG. 6.

One problem with prior sensor constructs arises from the fact that the light emitted from standard LEDs used as light sources is not at a pure wavelength, but includes a significant amount of light emission at longer wavelengths, which may reduce the quality of the measurement signal obtained. For example, a standard blue LED provides a 460 nm wavelength emission, but because of various factors, including factors involved in the manufacturing process, there is a significant amount (e.g., approximately 0.1% or more of total emission) of light emission spreading into the red region (e.g., above 600 nm) of the spectrum. The red-doped epoxy material 107 acts as a filter to block the blue wavelengths from being incident on the photodetector 103, but cannot filter out such so-called "red-tail" emissions from the LED light source.

Figure 3A:
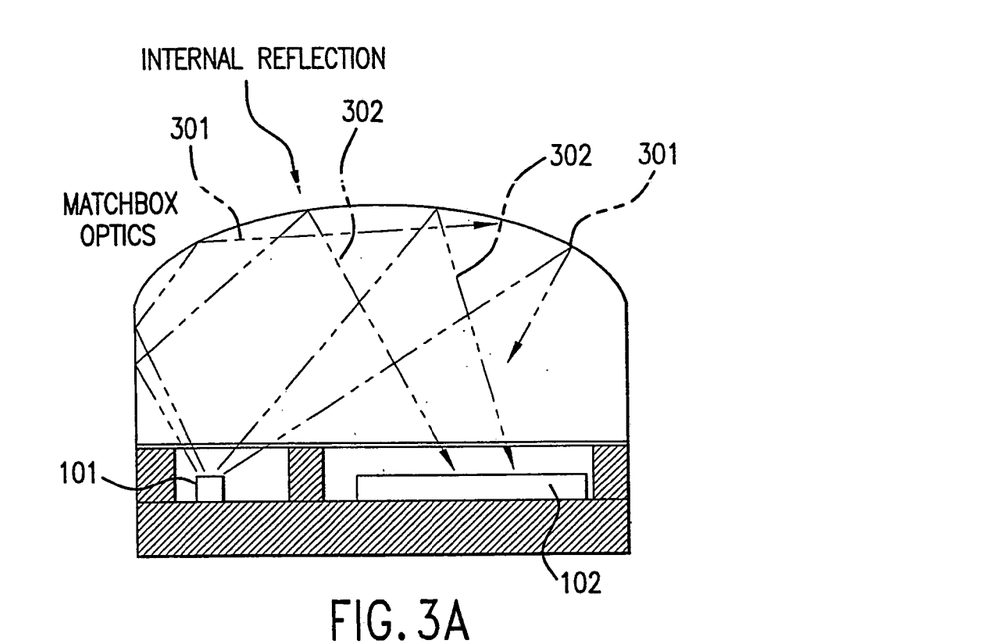
FIGS. 3A and 3B are side views illustrating the problem of emission of light noise from a light source of an optical sensor, and the solution achieved by the present invention, respectively.

In the case of an oxygen sensor device using ruthenium biphenyl phenanthroline as an indicator matrix, the peak emission of such indicator is 613 nm. Thus, the "red tail" emission of the LED contaminates the signal from the indicator. This "red tail" emission causes the signal baseline to be elevated and thereby suppresses the useful readable modulation of fluorescence emission from the indicator. This is shown in FIG. 3A.

Figure 3B:
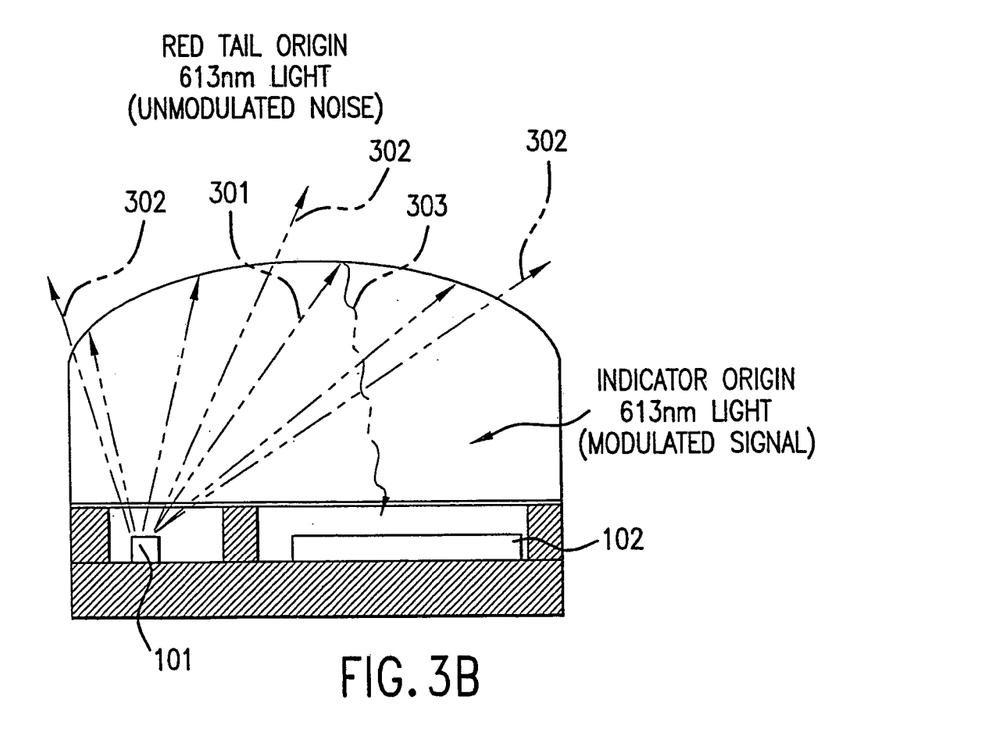

As shown, blue wavelength light emissions 301 (desired) are accompanied by extraneous, unwanted red wavelength emissions 302, which can be reflected by the prior waveguide construct to the detecting surface of the photodetector 102. According to the direct illumination construct of the present invention, most of the unwanted red wavelength emissions 302 from the LED light source are not reflected at the surface of the waveguide back to the photodetector, but instead pass directly out of the waveguide, such that substantially only red wavelength fluorescence emissions 303 in response to excitation from the blue wavelength light waves 301 impinges on the photodetecting surface of the photodetector 102. According to experimental measurements, baseline noise is reduced by more than 40 times the level produced by the prior geometry (e.g., from 23 mV to less than 0.5 mV). Additionally, as discussed above, the use of a blue-doped fill-in material in the light source cavity can aid in reducing "red-tail" emissions from the light source.

The simplest and most efficient configuration of the optical sensor device according to the invention is to have a flat surface for the waveguide, as shown in FIGS. 1A–1B, and 2A–2B. It also is possible to have a curved surface, as shown at in FIG. 4. Additionally, it is possible to have other surface geometries such as a sawtooth, gable, or inverse surface pattern, in order to increase surface area and thereby increase the amount of indicator available for analyte interaction.

Figure 4:
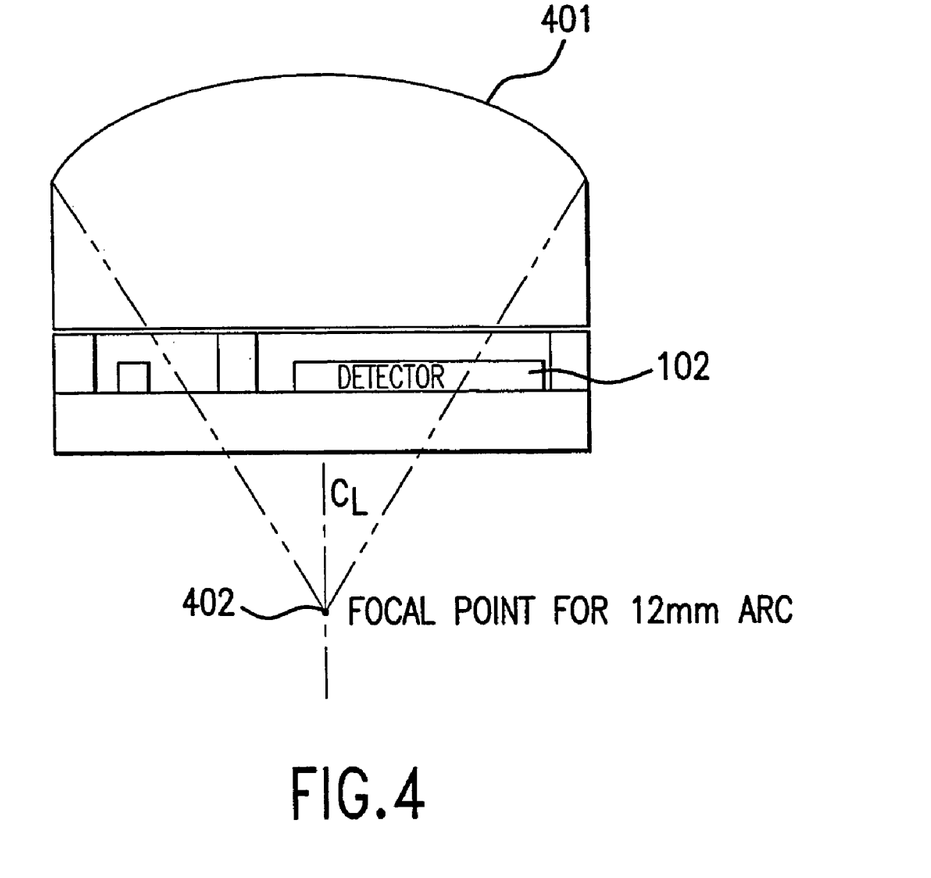
FIG. 4 is a side view illustrating the use of a curved waveguide surface for an optical sensor according to an alternate embodiment of the invention.
Figure 5A:
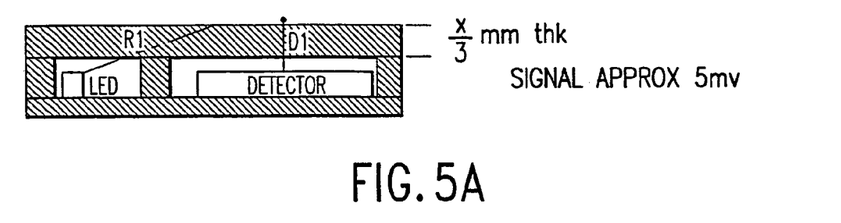
FIGS. 5A–5D are side views illustrating the optimization of waveguide thickness for the sensor device according to the present invention.
Figure 5B:
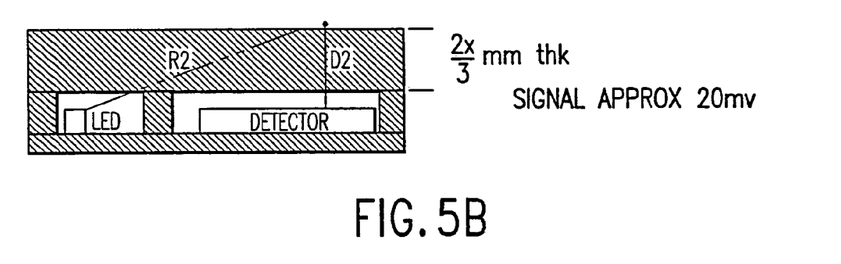
Figure 5C:
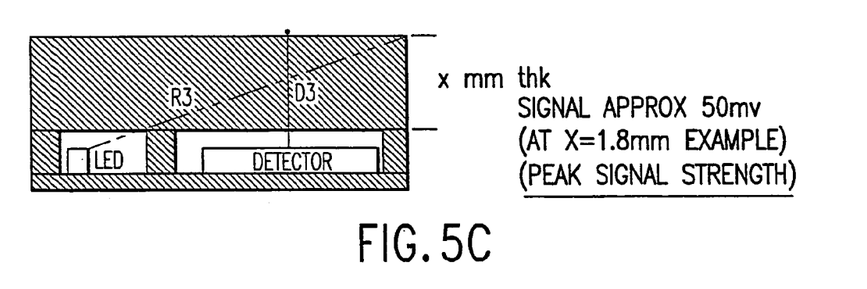
Figure 5D:
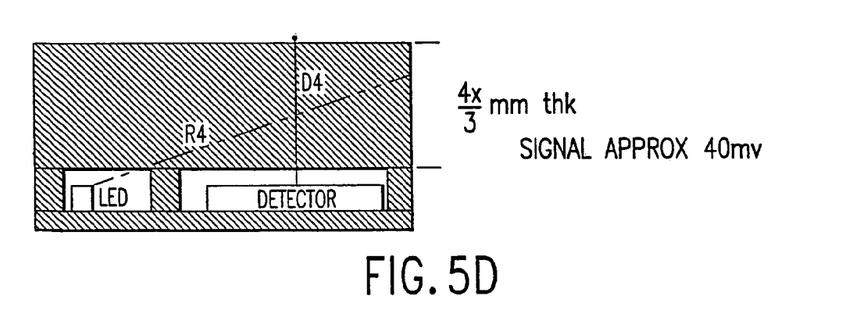

With the prior designs, it was thought that the curved arc of the waveguide played a role in focusing of the signal light onto the photodetector. To the contrary, internal reflectance or focusing are not significant phenomena according to the design of the present invention. As shown in FIG. 4, the focal point 402 of the arc has no relationship to the detector 102, and in fact is completely outside of the sensor device altogether.

Experimental observations and measurements have confirmed that the predominant amount of indicator light is produced in response to only direct illumination from the light source, as opposed to internally reflected light.

FIGS. 5A–5D illustrate a number of different waveguide thickness optimizations in light of the discovery that reflectance is not a major contributor to signal strength. As shown, various waveguide thicknesses were fabricated, where the thickness is characterized as a proportion of the distance from the LED light source to the intersection of the far field emission point X of the LED light source with the waveguide surface. For each thickness, signal strength was measured at a fixed LED current and amplifier gain. As illustrated, for a waveguide thickness of X/3, a signal of approximately 5 mV was produced; at 2X/3, a signal of approximately 20 mV was produced; at X, a signal of approximately 50 mV was produced; and at 4X/3, a signal of approximately 40 mV was produced. From these results, it can be seen that the peak signal strength is obtained when the thickness of the waveguide is set equal to X; in other words, where the far field emission point of the LED light source coincides with the corner of the waveguide. This may be achieved by appropriate relative positioning between the light source and the baffle, by selection of a light source with a particular intrinsice emission profile geometry, or by a combination of these factors.

Where the surface of the waveguide is made other than flat in order to obtain an increased surface area, the thickness X is equal to the mean height of the surface pattern as measured from the lower surface of the waveguide.

The optical sensor device according to the invention also may be configured as a dual or multi-detector, with photodetectors mounted on either side of the LED, and different indicator matrices disposed over each respective photodetector, such that the same excitation wavelength of the LED may excite different fluorescence wavelengths in each indicator matrix. Alternatively, multiple LEDs may be used, wherein each LED emits a different excitation wavelength causing a different fluorescence wavelength response.

Further, while refractive index matching has been described according to one preferred embodiment of the invention, it also is possible to select different refractive indices for each of the light source fill-in material, the waveguide material, and the photodetector fill-in material. It is known that light naturally travels from a medium having a lower refractive index to a medium having a higher refractive index.

Accordingly, since it is desired for excitation light to travel from the light source to the indicator matrix disposed on the waveguide surface, and for fluorescence light emission to travel from the indicator matrix to the photodetector, an alternate embodiment of the invention would provide successively higher indices of refraction for the light source fill-in material, the waveguide material, and the photodetector fill-in material.

The invention having been thus described, it will be apparent to those skilled in the art that the same may be varied in many ways without departing from the spirit and scope of the invention. For example, while the invention has been described with reference to a fluorescence sensor device for purposes of illustration, the principles of the invention may be applied to an optical sensor device using detection phenomena other than fluorescence. Any and all such modifications are intended to be encompassed by the following claims.

What is claimed is:

1. An optical sensor device for determining the presence or concentration of an analyte, comprising:
   a substrate;
   a light source for emitting light primarily of a preselected wavelength upon energization, mounted on a surface of said substrate;
   a light detector for detecting light incident thereon and generating an electrical signal responsive thereto, mounted on said surface adjacent to said light source;
   a waveguide formed over said light source and said light detector;
   an analyte-permeable indicator matrix disposed on an outer surface of said waveguide, said indicator matrix containing light-emitting indicator molecules whose light emission is attenuated or enhanced by the presence of analyte in said matrix, said indicator molecule being selected such that the wavelength emitted by the light source excites light emission in the indicator molecules; and
   a transparent fill-in material formed over said light source in a cavity in which said light source is located, wherein said transparent fill-in material has a refractive index that is substantially equal to the refractive index of said waveguide, such that said light source is in effect mounted within said waveguide;
   wherein said light detector generates an electrical signal responsive to light incident thereon emitted by said indicator molecules.

2. An optical sensor device according to claim 1, wherein said fill-in material is a polymeric material.

3. An optical sensor device for determining the presence or concentration of an analyte, comprising:
   a substrate;
   a light source for emitting light primarily of a preselected wavelength upon energization, mounted on a surface of said substrate;
   a light detector for detecting light incident thereon and generating an electrical signal responsive thereto, mounted on said surface adjacent to said light source, and being separated therefrom by a light shielding baffle, said baffle defining at least two cavities in which said light source and said light detector are located when mounted on said substrate;
   a waveguide formed over said light source, said light detector and cavities;
   an analyte-permeable indicator matrix disposed on an outer surface of said waveguide, said indicator matrix containing light-emitting indicator molecules whose light emission is attenuated or enhanced by the presence of analyte in said matrix, said indicator molecule being selected such that the wavelength emitted by the light source excites light emission in the indicator molecules; and
   a color-doped fill-in material formed over said photodetector in the cavity in which said photodetector is located, wherein said color-doped fill-in material functions as a filter to block a predominant wavelength emitted by said light source from impinging on said photodetector;
   wherein said light detector generates an electrical signal responsive to light incident thereon emitted by said indicator molecules.

4. An optical sensor device according to claim 3, wherein said color-doped fill-in material has a refractive index that is higher than the refractive index of said waveguide.

* * * * *